United States Patent [19]

Lennox, Jr.

[11] 4,196,055

[45] Apr. 1, 1980

[54] METHOD OF DETERMINING THE PRESENCE OF STRAY ELECTRICAL CURRENTS IN A SOLUTION

[75] Inventor: Thomas J. Lennox, Jr., Springfield, Va.

[73] Assignee: The United States of America as represented by the Secretary of the Navy, Washington, D.C.

[21] Appl. No.: 607,528

[22] Filed: Aug. 25, 1975

[51] Int. Cl.² ........................................... G01N 27/26
[52] U.S. Cl. .................................................... 204/1 T
[58] Field of Search .............................. 204/1 T, 1 C

[56] References Cited

U.S. PATENT DOCUMENTS

| | | | |
|---|---|---|---|
| 3,314,874 | 4/1967 | Flournoy | 204/1 C |
| 3,398,065 | 8/1968 | Marsh | 204/1 C |
| 3,616,415 | 10/1971 | Watson et al. | 204/1 C |

OTHER PUBLICATIONS

"Underground Corrosion", National Bureau of Standards Circular 579, Apr., 1957, p. 168.

*Primary Examiner*—G. L. Kaplan
*Attorney, Agent, or Firm*—R. S. Sciascia; Philip Schneider; Melvin L. Crane

[57] ABSTRACT

A system and method of detecting stray electrical currents that cause corrosion on metallic structures submerged in electrolytic media. The system makes use of a plurality of metal plates in an arrangement so they will be bipolar electrodes in a stray current field and the stray currents are determined by the color of the plates. The amount of stray currents are determined by the amount of metal loss over a period of time. Plates may be placed about a ship's hull, or other submerged structures, or suspended in an open area of solution to locate areas of stray currents.

4 Claims, 3 Drawing Figures

METHOD OF DETERMINING THE PRESENCE OF STRAY ELECTRICAL CURRENTS IN A SOLUTION

BACKGROUND OF THE INVENTION

A method and system of detecting and measuring dc stray electrical currents in an area which causes corrosion to an object in the area.

It is well known that direct current (dc) stray currents have a deleterious effect on metals submerged in water, especially sea water as well as those buried in the ground. Where dc stray current is picked-up by a metal from the water, corrosion will not occur unless the metal is amphoteric such as aluminum, zinc or lead. At the area where the current leaves the metal to return to the water to seek its source, accelerated and catastrophic corrosion can occur. In sea water, and in other water such as in harbors, metallic ship hulls and other metallic structures have been known to catastrophically corrode requiring extensive repairs. The cause of such accelerated corrosion has been attributed to the existence of dc stray electrical currents flowing in the water.

A common method used in attempts to detect stray dc electrical currents in water or other electrolytic media is by monitoring (recording) over a period of time the potential (voltage) of the metal whose corrosion is accelerated. Fluctuations in voltage indicate the presence of stray currents. Such measurements may be made using a reference electrode such as a silver/silver chloride (Ag/AgCl), a saturated calomel electrode (SCE), or a saturated copper/copper sulfate (Cu/CuSo4). Use of this method assumes that the electrode potential of all metals behave in some sort of pattern in stray electrical current fields. This is not the case, particularly with an amphoteric metal such as aluminum where one cannot determine from electrode potential measurements whether the metal is corroding as an anode or being protected as a cathode.

An alternate method commonly used to detect stray electrical current in water or other electrolytic media is to determine the electrical current flow and the direction of the current flow in the water or media. In this instance, two or more of the same types of reference electrodes are spaced some distance apart in the water and the voltage between the spaced electrodes is measured. The difference in voltage so measured, if any, is a measure of the voltage drop as a result of current flow through the water. The direction of current flow is obtained from an analysis of the voltage differences so measured. Such a determination is only practical if a very large stray electrical current is present and/or the electrodes can be spaced many feet apart.

Heretofore metallic surfaces exposed to a corrosive electrolytic environment have been protected cathodically. In conventional cathodic protection systems for mitigating the corrosion of submarine or subterranean metallic structures, cathodic protection is attained by connecting sacrificial anodes of a metal with a more negative galvanic potential than the structure, such as magnesium, zinc, or aluminum alloys in the case of ferrous structures, to the structure and disposing them within the electrolytic environment. Also, direct current electricity can be supplied to the structure through inert or consumable impressed current anodes to provide all or part of the electrical current required for cathodic protection. Less expensive metals, such as scrap iron, can also be utilized as anodes where an auxiliary current source is used to drive current from the anode to the structure being protected. Cathodic protection of the structure is achieved when cathodic areas of the structure receive all electrons utilized in the cathodic process from the auxiliary anode, and not from the local anodes of the structure itself.

SUMMARY OF THE INVENTION

This invention makes use of copper-base alloy coupons or plates which contain a high percentage of zinc; i.e., the classification of alloys generally considered not resistant to dezincification particularly the copper-base alloy normally referred to as yellow-brass, 64 parts copper and 36 parts zinc, or CA No. 268, a Copper Development Association Alloy designation which has been found to be especially useful in detection of stray direct electrical currents. By obtaining weight loss data on the yellow-brass coupons, the magnitude of the stray electrical currents can be determined. When there are stray electrical currents in sea water, yellow-brass will dealloy at an extremely rapid rate. The detection of stray dc current is evident by the color of the coupon and the side which is discharging the stray current into the water will obtain a relatively uniform metallic copper (reddish) color in contrast to the yellowish or gold color of the yellow-brass which is not exposed to dc stray currents or is the cathodic area of the bipolar electrode in a stray current field. This color change method can detect a stray direct electrical current density of 5 mA/sq.ft. which is well below the dc current density where catastrophic corrosion will occur.

DETAILED DESCRIPTION

Figure 2:
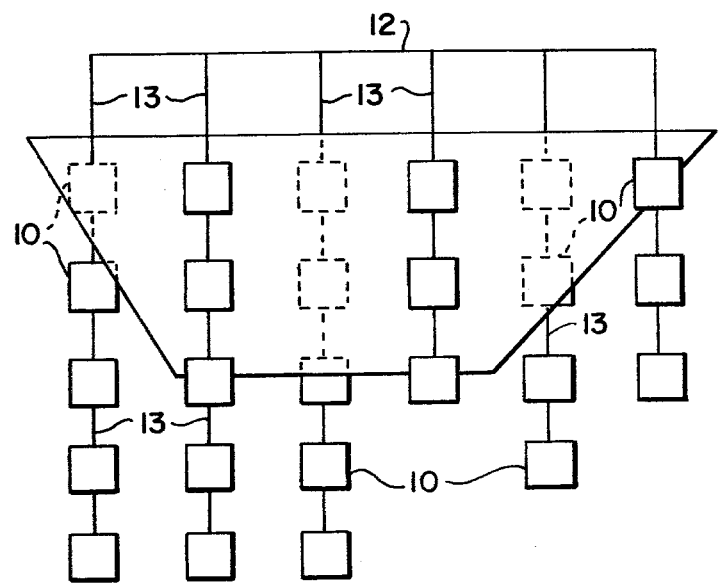
FIG. 2 illustrates a plurality of plates suspended in the water along side a ship on both sides.
Figure 3:
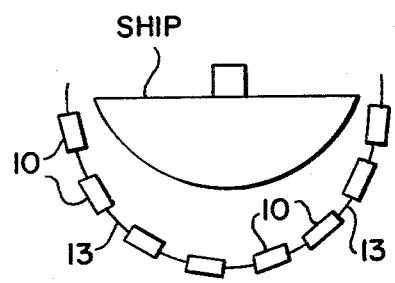
FIG. 3 illustrates a plurality of plates secured around the hull of a ship from one side to the other equidistant from the hull.

Now referring to the drawing, there is shown for illustrative purposes a yellow-brass (CA No. 268) or other suitable metal or alloy plate 10. The plate is provided with at least one aperture near one end so that the plate may be suspended from a support line frame attachment or any other suitable means 12 by use of non-conductive suspension rig 13 such as a rope, fiber, insulated wire, etc. If a metallic wire or wire rope is used for the support and or suspension rig, they must be insulated electrically from the yellow-brass plate. The aperture through which the plate is suspended is sealed by use of a water proof seal 14 so that no water gets into the area of the aperture thereby preventing extraneous galvanic effects that could cause corrosion. The opposite end of the plate may be provided with an aperture 15 sealed as described above and suspended at or near a surface such as a ship's hull as shown in FIGS. 2 and 3. The more nearly the plate is parallel with the surface to be checked the more accurate the determination.

In FIG. 2, a plurality of plates are suspended and secured near the outer surface of a ship's hull along each side and the ends thereof in straight lines with the upper most plate suspended from a support line with additional plates suspended by a rig from the above adjacent plate at various water depths. In this view, the plates are hanging one from the other and are suspended to a depth below the bottom surface line. FIG. 3 illustrates adjacent plates secured to each other with the plates forming a series of bands suspended near the side and bottom surfaces of a ship. In FIG. 3, the stray electrical currents would be detected along the entire hull surface. In the arrangement shown in FIG. 2, stray currents on the bottom surface probably would not be detected.

In order to differentiate between the side or area of a ship or other structure which is picking up a dc electrical current, that is, where corrosion will not occur, and the area of the ship of structure discharging current into the water, that is, areas where catastrophic corrosion could occur, it is essential that the metallic plates or detectors be orientated parallel with and near to the surface of concern.

For a general stray current survey in an area not specifically associated with a particular ship's hull or other existing structure, a plastic float or other suitable means from which the plates or coupons can be suspended using a variety of plate orientations and depths can be used to detect stray currents.

With such arrangements, the direction of the current flow can be determined as well as the magnitude of the electrical current. The direction of the electrical current flow is determined by the color of the plate. It has been determined that the side of the plate which is discharging an electrical current will attain a relatively uniform metallic copper (reddish) color in contrast with the normal yellowish (gold or brassy) color of the yellow-brass which is not exposed to stray electrical currents in the same environment. In order to determine the magnitude of the stray electrical currents, the plates are weighed before placing in the environment and then subsequently weighed after removal from the environment to measure the difference in weight. The difference in weight is used as a measure of the dc electrical current flow. Yellow-brass plates as set forth herein will dealloy at an extremely rapid rate, generally in two days, or less, when in a stray direct current electrical field. Also, the presence of a stray dc electrical current may be determined in a relative short time after immersion of the plates by visually observing the color change which takes place. The color change will take place for all stray electrical currents when the current density is 5 mA/sq.ft. or greater.

Figure 1:
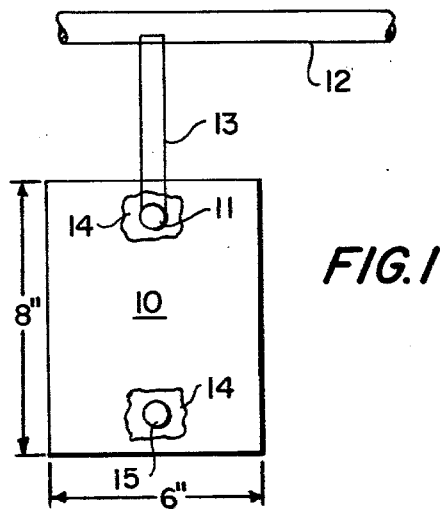
FIG. 1 illustrates a representative plate suitable for use in stray direct electrical current detection.

The dimensions of a representative plate have been given on FIG. 1. The size is not too important since the plates may be of any desired size; however, they need to be rigged for securing a plurality of plates in the water which will restrict their size. Any suitable rigging is acceptable however care should be exercised to avoid galvanic or electrical coupling to the rigging or suspension lines. The plates must be isolated, floating, electrodes without any electrical connections to the structure of concern or to adjacent plates. The plates must be suspended in the area of interest and at least one surface or part of one surface of the plate must be exposed to the surrounding environment such as sea water, brackish water or any other solution of concern. If a metallic rope is used for rigging the plates, the junction at the plates must be isolated from the water to prevent galvanic effects that could cause corrosion or protection of the plate. The plates should also be electrically isolated from each other to prevent artifacts.

This invention is not limited to the use of yellow-brass plates which contain zinc as the principle alloying metal since other alloying elements such as nickel, aluminum, tin, lead, silicon or any other metals and alloys, which show a change in color and appearance when placed in a solution where stray currents are present compared to their changes in color and appearance when they are placed in the same type of solution in which stray currents are not present, are visualized as effective. Electrodes on which such color changes and appearance changes occur may be anodes, bipolar anodes, cathodes, or bipolar cathodes.

Yellow-brass is the preferred alloy for stray electrical current detection because it is more resistant to marine fouling growth. In time, the appearance of white to green color salts on the yellow-brass surface are evident. These colored salts will remain on the surface of the yellow-brass unless they are removed mechanically or by rinsing and scrubbing in water. The metallic copper (reddish) color will remain on the plates even after they are cleaned chemically by ASTM Standard Practices for Preparing, Cleaning, and Evaluating Corrosion Test Specimens (ASTM designation G1-72). The color changes so described are evident at all electrical current densities of at least 5 mA/sq.ft.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A method of determining the presence of stray electrical currents near an object in a liquid, electrically conductive environment comprising the steps of:
   rigging at least one flat copper-alloy plate in said environment with a flat surface spaced from but substantially facing said object, the plate being free from galvanic coupling to the rigging, and free from any externally applied electrical potential or current,
   the plate material being of the type which reacts to the presence of a stray electrical current within said environment by a change in its color, and
   determining whether a color change occurs on said plates.

2. A method of determining the presence of stray electrical currents near an object in a liquid, electrically conductive environment comprising the steps of:
   rigging a plurality of flat copper-alloy plates in said environment with the flat surfaces spaced from but facing and substantially parallel to the surface of said object, the plates being free of galvanic coupling to each other and to the rigging and free from any externally applied electrical potential or current,
   the plate material being of the type which reacts to the presence of a stray electrical current within said environment by a change in its color, and a change in color of any one of said plates indicating a stray electrical current within said environment, and
   determining whether a color change occurs in any of the said plates.

3. A method of determining the presence of stray electrical currents near a structure suspended in a liquid, electrically conductive environment comprising the steps of:
   rigging a plurality of flat copper-alloy plates in said environment such that the plates are spaced from each other and said structure completely surrounding said structure within said environment with one flat surface of each plate facing said structure substantially parallel to the surface of said structure, electrically isolated from said structure, free of galvanic coupling to each other and to the rigging, and free from any externally applied electrical potential or current;

the plate material being of a type which reacts to the presence of a stray electrical current within said environment by a change in its color, and a change in color of any one of said plates indicating a stray electrical current within said environment.

4. A method as claimed in claim 3 wherein:

said plates are rigged such that they are parallel with the adjacent surface of said structure and spaced therefrom on all sides.

* * * * *